United States Patent [19]

Elliott et al.

[11] 4,009,413

[45] Feb. 22, 1977

[54] PLASMA JET DEVICE AND METHOD OF OPERATING SAME

[75] Inventors: William G. Elliott, Lincoln; Thomas J. Karlinski, Brookline, both of Mass.

[73] Assignee: SpectraMetrics, Incorporated, Andover, Mass.

[22] Filed: Feb. 27, 1975

[21] Appl. No.: 553,572

[52] U.S. Cl. .......................... 315/111.2; 219/121 P; 313/231.4; 356/86

[51] Int. Cl.[2] .......................... G01J 3/30; H05H 1/00

[58] Field of Search .......................... 313/231.3, 231.4; 315/111.2; 219/121 P; 356/85, 86

[56] References Cited

UNITED STATES PATENTS

| | | | |
|---|---|---|---|
| 3,242,798 | 3/1966 | Yamamoto | 356/85 |
| 3,424,533 | 1/1969 | Hughes et al. | 356/85 |
| 3,484,650 | 12/1969 | Rendina | 313/231.3 X |
| 3,558,227 | 1/1971 | Tlalka | 356/86 |
| 3,596,128 | 7/1971 | Elliott | 315/111.2 X |
| 3,736,059 | 5/1973 | Schuhknecht et al. | 356/86 |
| 3,770,935 | 11/1973 | Tateno et al. | 219/121 P |
| 3,783,227 | 1/1974 | Aitken | 219/121 P |

FOREIGN PATENTS OR APPLICATIONS

| | | | |
|---|---|---|---|
| 1,469,629 | 1/1967 | France | 315/111.2 |

*Primary Examiner*—Palmer C. Demeo
*Attorney, Agent, or Firm*—Richard P. Crowley

[57] ABSTRACT

A plasma jet device which comprises an anode electrode and a cathode electrode to provide an ionized gas column therebetween, the anode and cathode electrodes positioned such that their axes, if extended, would intersect at an angle, the ionized gas characterized by an inverted V form and a reaction zone in the region of intersection of the extended axes, and an external means to introduce a material to be observed directly into the reaction zone.

18 Claims, 4 Drawing Figures

PLASMA JET DEVICE AND METHOD OF OPERATING SAME

BACKGROUND OF THE INVENTION

Plasma jet devices, such as those of the direct current discharge type, which provide as ionized gas, are useful for generating excitation for spectrometric analysis or for studies of high-temperature chemical and physical phenomena of various materials.

U.S. Pat. No. 3,596,128, issued Jul. 27, 1971, describes an excitation source useful, for example, in spectroscopic analysis wherein a plasma jet device includes a swirl chamber surrounding an anode electrode and wherein a premixed atomized sample to be observed and an ionizing carrier gas is introduced into the chamber. In such plasma device and method, the plasma flame was directed through an orifice in the chamber, and the plasma flame bent to engage the cathode electrode at an angle to the axis of the plasma column. Although such a plasma device as described provided substantial improvement over prior art plasma devices, it has become apparent that there are certain difficulties associated with this device.

One of the difficulties involves the transport of the preatomized sample from the atomizing chamber to the swirl chamber surrounding the anode electrode. Other inherent problems in the use of a swirl-type chamber include the build up of aerosol particles within the chamber, and contamination of the exit port of the chamber with vapors of some of the elements to be observed; notably boron. In addition, studies have indicated that tangential introduction into the swirl chamber with subsequent uniform distribution of the sample surrounding the plasma through the exit port was highly inefficient in terms of the fraction of the sample to be observed actually reaching the region of maximum excitation of the sample; that is, the inner radius of the bend in the plasma column.

The patented plasma jet device discussed above, as well as a plasma device wherein the anode and cathode electrodes are positioned such that their axes, if extended, would intersect at an angle, has been discussed in an article "The Design and Some Emission Characteristics of an Economical dc Arc Plasmajet Excitation Source for Solution Analysis, " S. E. Valente and W. G. Schrenk, *Applied Spectroscopy*, Volume 24, Number 2, March - April 1970, pages 197–205. This publication discusses the introduction of samples to be observed in a plasma jet device which comprises anode and cathode electrodes, each coaxially surrounded by a sleeve element through which an ionizing gas is introduced to form an inverted V-type ionized gas. Sample material to be observed in the excitation source was introduced coaxially through the anode sleeve. However, in such device and by such technique, the sample material contaminates the sleeve element through which it is introduced. Thus, as in the patented plasma device, such technique of introduction is highly inefficient in terms of the fraction of the sample which actually reaches the region of maximum excitation. Further, such method of introduction of the sample fails to achieve good penetration of the sample into the sheath surrounding the ionized gas, with the result that the emission intensity distribution of the sample is not wholly satisfactory. Accordingly, there is a need for a plasma jet device which overcomes the difficulties associated with such prior art devices and techniques of sample introduction.

SUMMARY OF THE INVENTION

Our invention concerns an improved plasma jet device and a method of operating and using such device for the observation of materials. In particular, our invention relates to a plasma jet device characterized by an inverted V-type ionizing gas discharge, and a means of introducing material to be observed directly into the reaction zone of the plasma.

Our plasma jet device comprises in combination: an anode electrode and a cathode electrode, the anode and cathode electrodes positioned such that their axes, if extended, would intersect at an acute angle, typically from about 60° to 90°; means to introduce an ionizable gas between the anode and cathode electrodes to form a plasma jet comprising ionized gas therebetween, with the discharge characterized by an inverted V shape or form; e.g., with a bend or reaction zone at the region of intersection of the extended axes of the electrodes; and, importantly, an external means to introduce the material to be observed directly into the reaction zone of the intersection of the plasma jet.

The material to be analyzed, observed or studied, either in solid, liquid, vapor, gaseous, aerosol or other form, is introduced directly into the region of the intersection. Preferably, the material is introduced by discharging the material in finely divided aerosol form vertically and upwardly directly into the lower portion of the intersection region. By such technique and means, the material introduced does not come into proximity with either of the electrodes and does not pass through a constriction together with the plasma jet gas. By such means and technique, there is no possibility of contamination of either the constricting member, such as an exit port or sleeve element, as in prior art devices, or of either of the electrodes. Our invention avoids the possible premixing of the carrier gas of the aerosol with the ionizable gas to form the plasma discharge. We have found that enhanced and improved sensitivity is achieved because of this method of introduction, since the material is introduced only into the region of intersection and is not distributed uniformly around the plasma column. Our invention provides for a much greater percentage of the material to be introduced and to experience the maximum excitation environment.

We have found also that introduction of a sample material into the region of intersection, and more particularly into the lower portion of the region defined as a "reaction" zone, is particularly beneficial in that such direct sample introduction provides for better and more efficient excitation of the material and improved penetration into the sheath region by the sample when the sample is introduced into the reaction zone. Although not wishing to be bound by any particular theory, it is believed that such improved material penetration into such sheath in such reaction zone may be the result of differences in pressures involved within and about such region. Our invention of introducing the sample provides many improvements and advantages over the prior art plasma jet devices and sample introduction methods and techniques.

DESCRIPTION OF THE EMBODIMENTS

Figure 1:
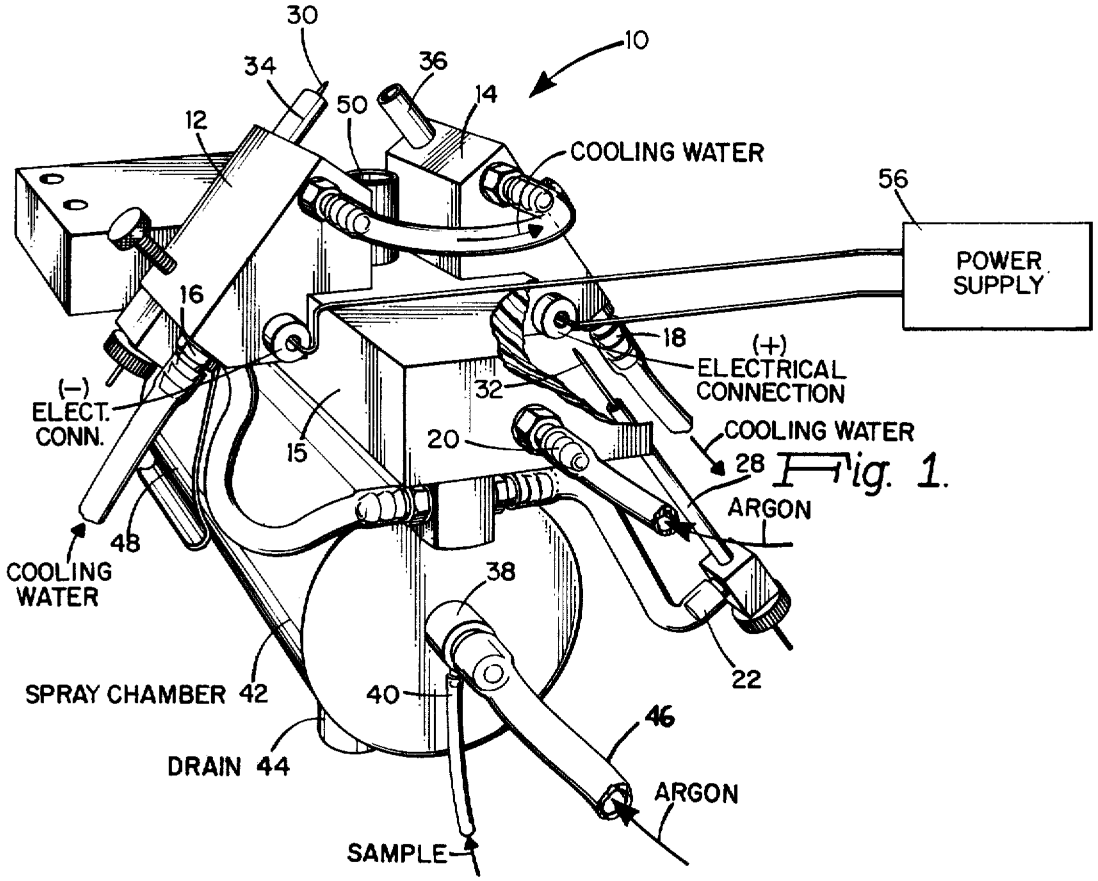
FIG. 1 is a perspective view of the plasma jet device of our invention with a partially exploded view of one electrode.
Figure 2:
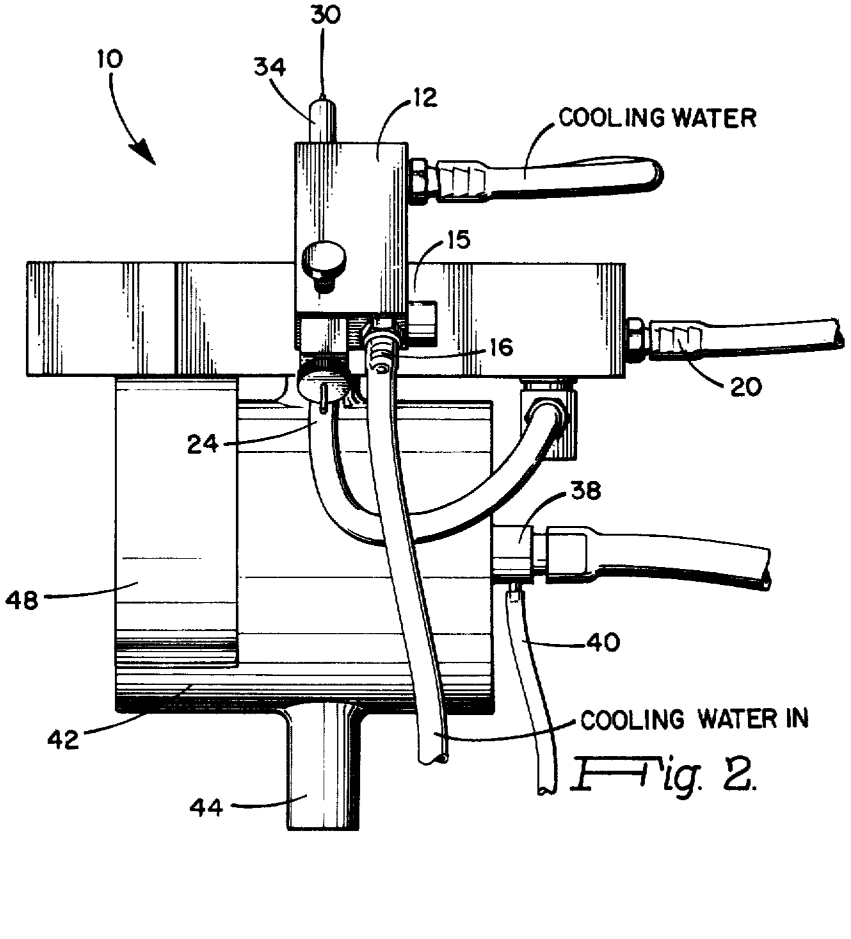
FIG. 2 is a side elevation view of the device of FIG. 1.
Figure 3:
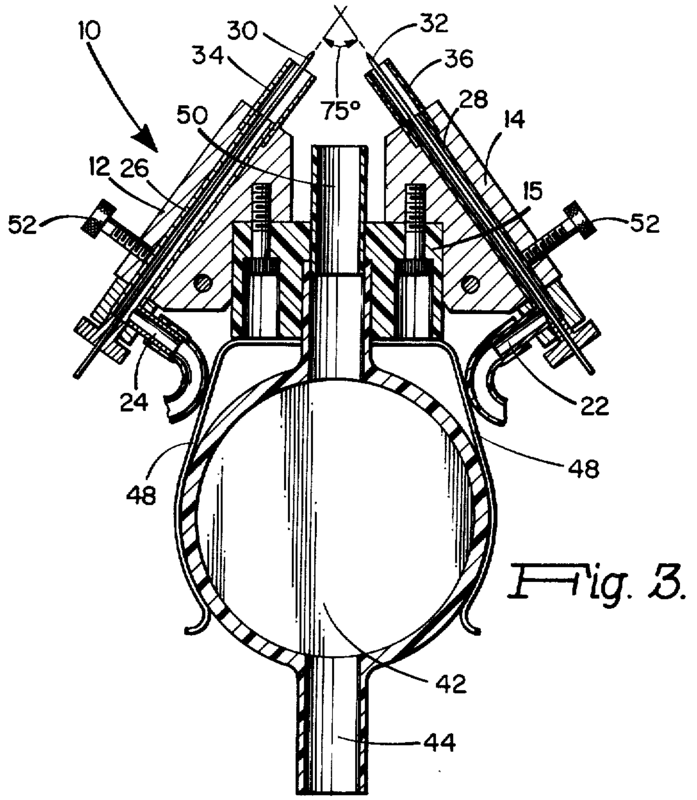
FIG. 3 is a cross-sectional view of the device of FIG. 1.

Our plasma jet device 10, referring particularly to FIGS. 1–3, comprises a pair of stainless steel water-cooled electrode holders 12 and 14 mounted on a solid insulating block 15. A cooling water entrance port 16 is threaded into one electrode holder and a cooling water exit port 18 into the other to provide for the circulation of cooling water through each holder 12 and 14. The block 15 includes an ionizable main gas entrance port 20, gas entrance anode port 22 and gas entrance cathode port 24 connected with associating tubing to provide for the introduction of an ionizable gas, such as argon from a source (not shown) and into the port 20, and its distribution to each of the electrode holders. The anode and cathode electrodes comprise cathode 26 and anode 28 stainless steel tubing elements, such as a stainless steel tube of about 4.5 cm long and 0.3 cm in diameter. A cathode 30 and an anode 32 electrode rods having a diameter of about 0.1 cm composed of a zirconium-doped tungsten material, are positioned coaxially in the center of each of the tubing elements 26 and 28, respectively, to form each electrode assembly. A threaded screw is provided to secure in an axially movable fashion each electrode rod within its respective electrode tubing element. The gas anode and gas cathode entrance ports 22 and 24 are part of each assembly, and are positioned such as to introduce the ionizable gas coaxially into the interior of the cathode and anode tubing elements 26 and 28. As illustrated in particular in FIG. 1, one of the subassemblies with the electrodes is shown inserted into one of the electrode holders, while the other subassembly has been illustrated in an exploded view prior to insertion into the electrode holder.

The cathode 34 and anode 36 ceramic sleeve elements approximately 1.5 cm long and slightly greater than 0.3 cm in diameter are installed about the end of each of the electrode tubing elements 26 and 28 and into angular openings in the electrode holders 12 and 14, with approximately one-half the length of each of the ceramic sleeve elements extending into the water-cooled electrode holders, and the other half extending toward the region of intersection. The tip of each electrode 30 and 32 is positioned such that it is just inside the end of the respective ceramic sleeve elements 34 and 36. As illustrated, the anode and cathode electrodes 30 and 32 are positioned such that their axes, if extended (as illustrated by the dotted line in FIG. 3), would intersect at an acute angle between the electrode holders, forming an angle of approximately 75° which has been found to be the optimum and preferred angle in respect to the illustrated embodiment.

Restraining means, such as threadable thumb screws 52, are provided in each electrode holder in order to secure the electrode subassemblies of the anode and cathode tubing elements 26 and 28 in position within the electrode holders. Electrical connections in the insulating block lead to each electrode 30 and 32 and are electrically connected to a power source 56. In use, although not illustrated, the compact size of our plasma jet device permits it to be adapted for use with most commercial spectrometers and spectrographs. Typically, one electrode holder is connected to the positive outlet of a fast response, current-regulated, power supply via a high-frequency, spart-induction coil. The other electrode is connected to the negative outlet of the power supply 56. The supply under normal operating conditions is adjusted to regulate the current flow at a value of approximately 7 amperes. An ionized gas discharge or plasma jet is initiated by either extending the electrodes until they touch and then withdrawing them back within the ceramic sleeves 34 and 36, or by a high-frequency electric spark to ionize the plasma gas and to overcome the voltage drop at the electrode surfaces. In operation, a continuous plasma column of ionizable gas is generated extending between the respective ends of the electrodes and having an inverted V-shape and a bend near the intersection of the extended electrode axes, as illustrated more particularly in FIG. 4.

Below the insulating block is a spray chamber 42 composed of a cylindrical polypropylene chamber approximately 5 cm in diameter and approximately 7 cm long. Such chamber 42 includes at one end thereof a centrally disposed pneumatic nebulizer 38. The nebulizer 38 comprises a lower sample inlet port 40 and a gas nebulizer inlet port 46, wherein a gas is introduced through the port 46 to atomize the sample and provide an aerosol-containing sample of the material to be observed. The drain tube 44 is provided at the bottom of a chamber for draining any excessive liquid sample, while a cylindrical sample exit tube 50 is provided at the top of the chamber to carry the sample aerosol material formed by the nebulizer vertically upwardly and directly into the lower portion of the region of the plasma intersection. In operation, a back pressure, for example, of approximately 4 inches of water or greater, is provided in the drain line to insure that the aerosol exits through the sample exit tube 50 into the plasma instead of through the drain 44. The sample exit part is aligned and positioned such that the exit is just below the region of intersection of the plasma device.

The operation of our plasma jet device will be described in particular in connection with the analysis of a liquid sample material, wherein an aerosol containing the sample is generated through the introduction of a small amount of the liquid sample material through te sample port 40, while passing a carrier gas, such as argon, through the port 46 to nebulize the sample in nebulizer 38 and to form an aerosol containing finely divided liquid particles of material within the spray chamber 42. Any excess liquid sample is drained from drain 44, while the aerosol containing the sample moves vertically upwardly through the sample exit port 50 into the plasma intersection. The plasma is initiated by ionizing argon in the path between the electrodes to conduct current from the power supply. Heating of the argon due to the passage of the current ionizes additional argon introduced through the tubing elements 26 and 28 to sustain the plasma jet during operation.

Figure 4:
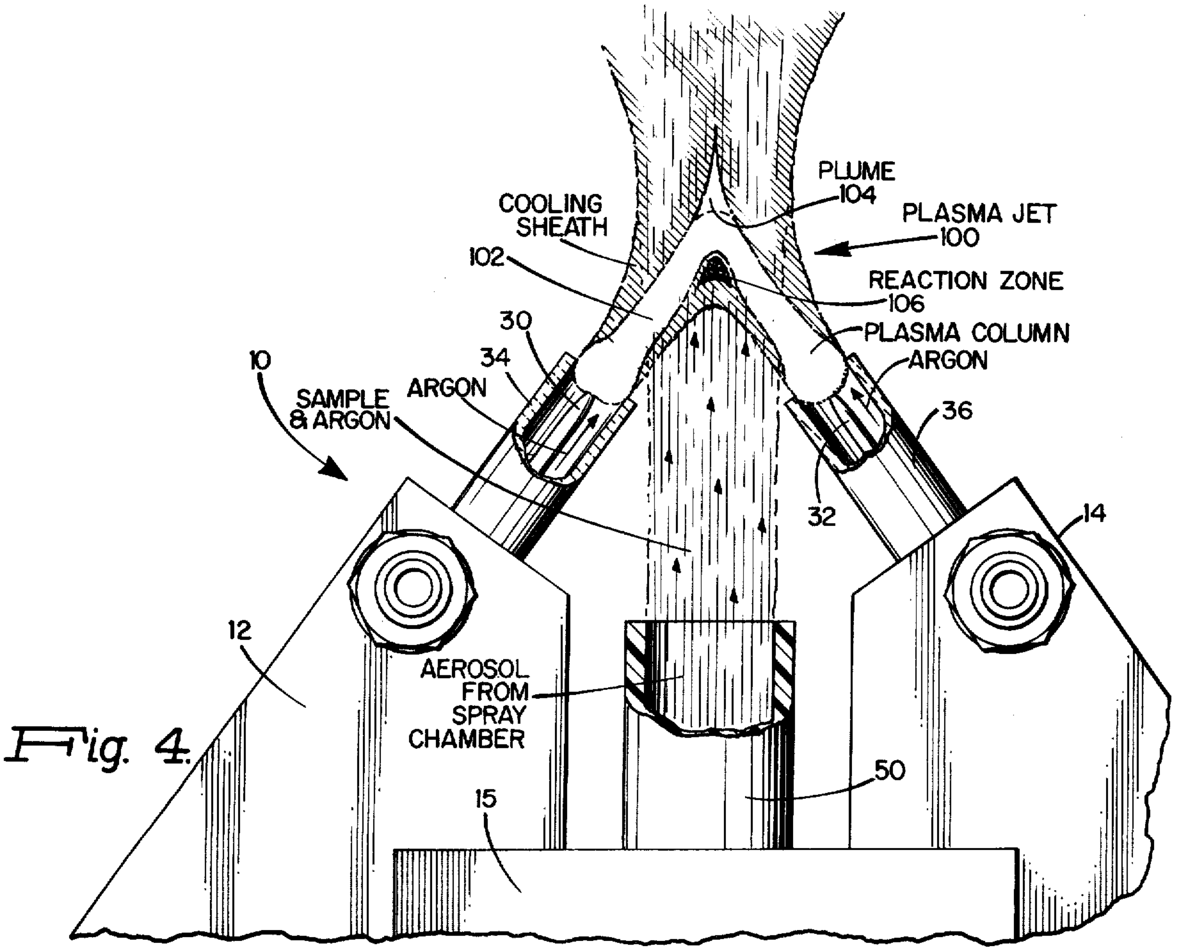
FIG. 4 is a schematic representation of the plasma jet device in operation.

FIG. 4 is a schematic illustration of our plasma jet device in operation, illustrating the introduction of the material into the plasma jet. The plasma 100 is generally illustrated as composing a tapered conical-like plasma column of ionized gas 102 extending from the end of each of the electrodes 28 and 30 and forming a region of intersection, the plasma jet characterized generally as an inverted V and having a plume 104 and an excitation or reaction zone region 106 directly beneath the region of intersection of the electrode axes. As illustrated, a sample material in aerosol form is introduced directly into the region of intersection beneath the plume 104 and into a region identified as an excitation or reaction zone region 106. The sample material then experiences an environment of excited electrons and ions in the sheath region surrounding the plasma. Energy is exchanged between these excited ions and electrons and the atoms or the molecules of the sample material introduced, which results in disassociation of molecules and the excitation of molecules and atoms. The sample material experiences effective temperatures in the range of approximately 4500° K to 7500° K, depending upon the volatility and ionization potential and the elements comprising the sample material.

We have found that the region at or about the inside radius or the plasma intersection or the lower portion of the inverted V (the reaction zone) provides the greatest density of sample atoms and greatest degree of excitation. In use, this region is viewed by a spectrometer or other instrument for performing spectroscopic analysis of the sample constituents. Of course, by our invention, other regions of the plasma jet may be viewed to obtain preferential excitation of certain elements, depending upon the atomic energy levels and ionization potentials of the atoms present. Therefore, advantage may be taken of the energy distribution of the samples to discriminate in favor or against specific constituents. In our plasma jet device, the sample material introduced is introduced directly into the reaction zone and excitation region, and does not come into proximity with either of the electrodes, and further, does not pass through any constriction. Our invention for introducing a sample provides for a higher percentage of the material to experience the excitation environment desired. Our plasma device, accordingly, avoids and solves many of the problems associated with prior art devices, while providing for more efficient sample introduction and high excitation of the sample. As illustrated, the sample is not introduced into the current-carrying or ionized column of the plasma jet which is not penetrated by the sample, but the sample is placed into the sheath of non-conducting gas or the cooling sheath surrounding the ionized column. Sample introduction into the cooling sheath at the reaction zone provides higher or more uniform excitations of the sample while near the bend, but not in the plasma column, there is very little background emission which provides for an excellent signal to background ratio.

Our plasma jet device has been described and illustrated in a particular embodiment for the purposes of illustration only, and it is recognized that various changes and modifications may be made in our plasma jet device and the technique of introducing the sample without departing from the spirit and scope of our invention. The introducion of the sample material has been illustrated particularly as the illustration of a liquid sample in aerosol form; however, it is recognized that the sample may be introduced in other forms and by other techniques. Our plasma jet device has also been illustrated employing argon as the ionizable gas to form the plasma jet. However, it is recognized that any ionizable gas may be employed, such as neon, helium or other inert ionizable-type gases; however, argon is the preferred ionizable gas. In addition, our plasma jet has been illustrated and suggested for use in spectrochemical analysis. However, it is recognized that the plasma jet may be employed in and with a variety of other devices to observe, analyze, test or otherwise treat materials in the high-temperature chemistry field.

What is claimed is:

1. A plasma jet device which comprises in combination:

a. an anode electrode;

b. a cathode electrode;

c. the anode and cathode electrodes spaced apart and positioned such that their axes, if extended, would intersect at an angle;

d. first and second coaxial sleeve elements surrounding the anode and cathode electrodes, respectively;

e. means to flow an ionizable gas through the first and second sleeve elements and about the electrodes to form in operation a plasma jet comprising a continuous column of ionized gas between the anode and cathode electrodes, the plasma jet characterized by an inverted V-form shape and a reaction zone in the plasma jet at the lower region of the intersection of the extended axes of the electrodes; and f. external and separate means to introduce a sample material directly into the reaction zone of the plasma jet.

2. The device of claim 1 wherein the anode and cathode electrodes are positioned such that their axes, if extended, would intersect at an angle of approximately 75°.

3. The device of claim 1 wherein the means to introduce the material into the plasma jet includes an external and separate sleeve element to direct sample material upwardly into the lower region of intersection and into the reaction zone of the plasma jet.

4. The device of claim 1 wherein the means to introduce the sample material includes:

a. a spray chamber;

b. a means to nebulize the sample material and to introduce the nebulized sample into the spray chamber; and c. upwardly extending sleeve means to introduce the nebulized sample from the spray chamber upwardly and directly into the reaction zone of the plasma jet.

5. The device of claim 4 wherein the means to nebulize the sample material includes means to introduce a liquid sample material and means to introduce an argon carrier gas into the nebulizer to form an argon aerosol of the sample material.

6. The device of claim 1 which includes a power supply and means to communicate electrically between the power supply and each of the electrodes.

7. The device of claim 1 wherein the means to position the ends of each electrode is slightly inside the ends of the respective elements.

8. A plasma jet device which comprises in combination;

a. an anode electrode;

b. a cathode electrode;

c. first and second coaxial sleeve elements respectively surrounding the anode and cathode electrodes;

d. means to flow an ionizable gas through the first and second sleeve elements and about the electrodes;
e. the anode and cathode electrodes positioned with respect to each other that their axes, is extended, would intersect at an angle of about 60 to 90° to form a plasma jet comprising a continuous column of ionized gas extending between the respective ends of the anode and cathode electrodes, and along the extended axes, the plasma jet characterized by an inverted V-form shape and a reaction zone near the lower region of intersection of the extended axes of the electrodes; and
f. external and separate means to introduce a sample material in aerosol form in an ionizable gas directly upwardly and into the reaction zone of the plasma jet.

9. A plasma jet device which comprises in combination:
a. an insulating block element;
b. a first anode and second cathode electrode holders mounted on the insulating block;
c. means to circulate a cooling fluid through the electrode holders;
d. cathode and anode electrode means positioned in respective electrode holders, and each comprising
i. an electrode rod element,
ii. a tubing sleeve element surrounding the electrode,
iii. insulating sleeve elements at one end of the electrode extending outwardly from the electrode holder,
iv. means to introduce an ionizable gas into the sleeve elements and about the electrode rod element, and
v. means to move the electrode rods axially within the sleeve element;
e. means to secure the cathode and anode electrode means in the electrode holders;
f. the electrode rods positioned such that their axes, if extended, would intersect at an angle to form a plasma jet comprising a continuous column of ionized gas between the ends of the electrode elements, the plasma jet characterized by an inverted V-form shape, and by a reaction zone in the lower region of the intersection of the axes;
g. a spray chamber positioned beneath the insulating block and characterized by an outlet to remove excess sample material, and a sample exit outlet, the sample outlet projecting as a sleeve element upwardly between the electrode holders and the exit directly below the reaction zone of the plasma jet;
h. a means to nebulize a sample material to be introduced into the plasma jet; and
i. means to introduce the nebulized sample into the spray chamber and upwardly through the exit outlet and directly into the reaction zone of the plasma jet.

10. In a method for introducing a sample material to be analyzed into a plasma jet of a continuous column of ionized gas extending between the ends of an anode electrode and a cathode electrode of an ionized gas, the anode and cathode electrodes spaced apart and positioned such that their axes, if extended, would intersect at an angle, wherein the plasma jet formed is characterized generally by an inverted V-form shape and a reaction zone in the region of intersection of the plasma jet, the improvement which comprises:
a. flowing an ionizable gas coaxially about and along each of the electrodes to form the continuous column of ionized gas; and
b. introducing a sample material to be analyzed from an external source directly into the inverted V-form area of the plasma jet formed between the ends of the electrodes.

11. The method of claim 10 which includes positioning the anode and cathode electrodes such that their axes, if extended, would intersect at an angle of approximately 75°.

12. The method of claim 10 wherein the ionizable gas is argon.

13. The method of claim 10 which includes nebulizing the sample material and introducing the nebulized sample material through an exit sleeve element positioned just below the inverted V form and into the reaction zone of the plasma jet.

14. The method of claim 13 wherein the sample material is a liquid material and the carrier gas is argon to form a liquid aerosol sample material.

15. The method of claim 10 which includes introducing the sample material directly into the reaction zone of the plasma jet.

16. The method of claim 10 which includes introducing the sample material as an aerosol material in an argon gas carrier.

17. The method of claim 10 which includes spectrometrically analyzing the excited sample material introduced into the plasma jet.

18. A method for generating a plasma jet between the ends of an anode and cathode electrode and introducing a sample material into the plasma jet for observation, which method comprises:
a. positioning the anode and cathode electrodes such that their axes, if extended, would intersect at an angle of approximately 60° to 90°;
b. flowing argon gas coaxially about the anode and cathode electrodes and along the extended axes thereof;
c. applying a voltage to the electrodes to form a plasma jet comprising a continuous column of ionized argon gas surrounded with a cooling sheath of argon gas, the plasma jet column formed along the extended axes of the electrodes, and characterized by an inverted V-form shape and a reaction zone at the lower region of the intersection of the axes; and
d. introducing from a separate source directly and upwardly a sample material to be observed in aerosol form into the lower portion of the reaction zone of the plasma jet.

* * * * *